(12) United States Patent
Fyrstén et al.

(10) Patent No.: US 11,707,544 B2
(45) Date of Patent: Jul. 25, 2023

(54) SANITIZING DEVICE AND SYSTEM COMPRISING THE SAME

(71) Applicant: Picote Solutions Oy Ltd., Porvoo (FI)

(72) Inventors: Keijo Fyrstén, Oulu (FI); Ville Hukkanen, Oulu (FI)

(73) Assignee: Picote Solutions Oy Ltd., Porvoo (FI)

( * ) Notice: Subject to any disclaimer, the term of this patent is extended or adjusted under 35 U.S.C. 154(b) by 282 days.

(21) Appl. No.: 17/217,042

(22) Filed: Mar. 30, 2021

(65) Prior Publication Data

US 2021/0308302 A1 Oct. 7, 2021

(30) Foreign Application Priority Data

Apr. 7, 2020 (FI) ..................................... 20205371

(51) Int. Cl.
*A61L 2/10* (2006.01)
*A61L 2/26* (2006.01)

(52) U.S. Cl.
CPC ................... *A61L 2/10* (2013.01); *A61L 2/26* (2013.01); *A61L 2202/11* (2013.01); *A61L 2202/17* (2013.01)

(58) Field of Classification Search
CPC ..... A61L 2/10; A61L 2/24; A61L 2/26; A61L 2/0047; A61L 2202/11; A61L 2202/14; A61L 2202/16; A61L 2202/17; B05B 13/0207; B05B 13/0214; B08B 9/023; A62C 33/02
See application file for complete search history.

(56) References Cited

U.S. PATENT DOCUMENTS

| | | | | |
|---|---|---|---|---|
| 4,280,672 A * | 7/1981 | Santos | ................... | B08B 9/023 242/537 |
| 4,734,950 A * | 4/1988 | Schenke | ................. | B08B 9/023 15/104.04 |
| 5,077,861 A * | 1/1992 | Bokat | ................... | A62C 33/02 15/88.1 |
| 5,356,480 A * | 10/1994 | Melgeorge | ............. | A62C 33/02 134/122 R |
| 5,630,436 A * | 5/1997 | Chase | ................... | A61B 1/125 134/169 R |
| 6,003,194 A * | 12/1999 | Eckroth | ................. | A62C 33/02 15/302 |
| 6,264,128 B1 * | 7/2001 | Shampine | ............ | B65H 75/425 242/157.1 |
| 6,487,750 B1 * | 12/2002 | Brown | ................ | B05B 13/0207 15/309.1 |
| 6,763,547 B1 * | 7/2004 | Brewer | .................. | A62C 33/02 15/309.1 |

(Continued)

FOREIGN PATENT DOCUMENTS

FI 123198 12/2012
WO 2018160974 9/2018

*Primary Examiner* — Sean M Luck
(74) *Attorney, Agent, or Firm* — Fasth Law Offices; Rolf Fasth

(57) ABSTRACT

A sanitizing device is disclosed that has a channel extending through the device. The sanitizing device has a coupler for attaching it to a sewer cleaning machine for running its cable and/or cover tube through the channel. A set of ultraviolet LEDs illuminate the channel and disinfect the cable or cover tube running through the sanitizing device. Also, a system including a power transmission device and the sanitizing device is disclosed.

3 Claims, 5 Drawing Sheets

(56) References Cited

U.S. PATENT DOCUMENTS

| | | | |
|---|---|---|---|
| 6,781,137 B2* | 8/2004 | Snowball | C02F 1/325 |
| | | | 250/455.11 |
| 6,990,707 B1* | 1/2006 | Heumann | B08B 1/02 |
| | | | 118/208 |
| 10,150,144 B2* | 12/2018 | Suiter | B08B 9/023 |
| 2003/0018373 A1* | 1/2003 | Eckhardt | A61N 5/0624 |
| | | | 607/94 |
| 2007/0234494 A1* | 10/2007 | Suzuki | A61B 1/125 |
| | | | 15/104.095 |
| 2007/0251039 A1* | 11/2007 | Kobayashi | A61B 90/70 |
| | | | 15/104.095 |
| 2008/0105625 A1* | 5/2008 | Rosenberg | B08B 3/12 |
| | | | 210/748.11 |
| 2008/0164422 A1* | 7/2008 | Kim | A61L 2/0088 |
| | | | 250/429 |
| 2009/0317293 A1 | 12/2009 | Street et al. | |
| 2014/0020716 A1* | 1/2014 | Suiter | B65H 57/14 |
| | | | 134/21 |
| 2014/0103228 A1* | 4/2014 | Waber | A61L 2/087 |
| | | | 313/42 |
| 2014/0255869 A1* | 9/2014 | Kanno | A61L 2/183 |
| | | | 433/29 |
| 2016/0288176 A1* | 10/2016 | Englent | E03F 9/002 |
| 2017/0022026 A1* | 1/2017 | Chapa | B65H 75/441 |
| 2017/0342700 A1* | 11/2017 | Wiedemann | B65H 75/425 |
| 2018/0319621 A1* | 11/2018 | Sevigny | B65H 57/14 |
| 2019/0038789 A1* | 2/2019 | Kang | A61L 2/16 |
| 2019/0117332 A1* | 4/2019 | Davis | A61J 15/0026 |
| 2019/0119065 A1* | 4/2019 | Timmer | B65H 75/28 |
| 2019/0176182 A1* | 6/2019 | Andersen | B05C 3/09 |
| 2019/0186673 A1* | 6/2019 | Martinsen | E21B 37/00 |

\* cited by examiner

US 11,707,544 B2

SANITIZING DEVICE AND SYSTEM COMPRISING THE SAME

PRIOR APPLICATION

This U.S. utility patent application claims priority from Finnish patent application no. FI20205371, filed 7 Apr. 2020.

FIELD AND SUMMARY OF THE INVENTION

The invention relates to a sanitizing device for sanitizing the outer surface of a tube using ultraviolet light.

The pipes in real estate properties are, increasingly more often, renovated by the so-called CIPP (Cured-in-Place Pipe) method, in which inside the pipes is installed an epoxy-saturated liner, which is slid into the pipe by the inversion method using air pressure. Before installation, the existing pipe has to be thoroughly cleaned. The existing pipe is typically a sewer pipe which is cleaned using a tool rotated with a cable running inside a cover duct. When the tool is removed from the existing pipe, the cover tube transfers bacteria, viruses and parasites from the sewer into contact with the user. As the equipment is transported away from the worksite, the bacteria, viruses and parasites from the sewer are also transported. This causes health problems, such as diseases and infections when the dirty equipment contaminates persons, vans and trucks, etc.

Currently, there is no viable solution for the problem. The equipment used in sewers is rinsed or disinfected every now and then but contamination happens between the cleanings.

The object of the invention is a device and a system, which alleviate the contamination problem of sewer cleaning devices of the prior art.

Object of the invention is achieved with a sanitizing device having a channel through the device. The sanitizing device has a coupler for attaching it to a sewer cleaning machine for running its cable and/or cover tube through the channel. A set of ultraviolet LEDs illuminate the channel and disinfect the cable or cover tube running through the sanitizing device.

BRIEF DESCRIPTION OF THE DRAWINGS

The invention is now described in more detail in connection with preferred embodiments, with reference to the accompanying drawings, in which.

DETAILED DESCRIPTION OF THE INVENTION

Figure 1A:
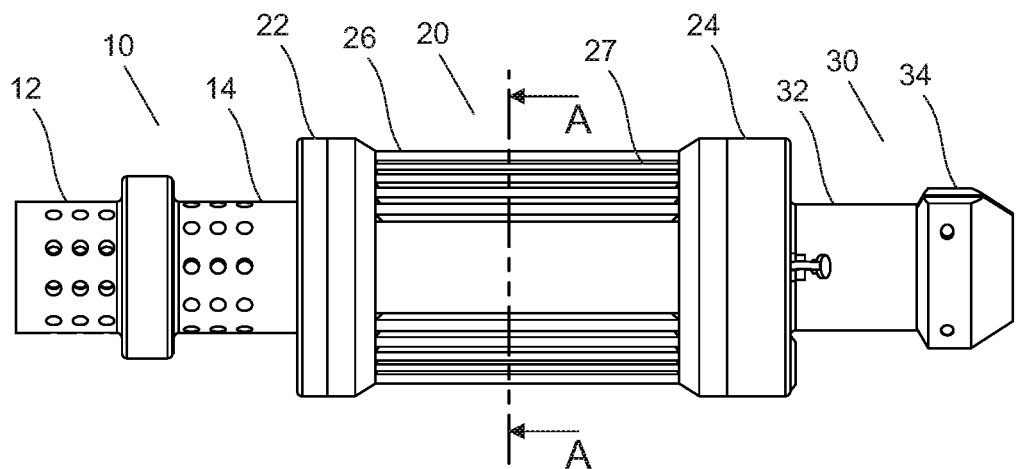
FIG. 1A shows a sideview of a sanitizing device according to an embodiment.
Figure 1B:
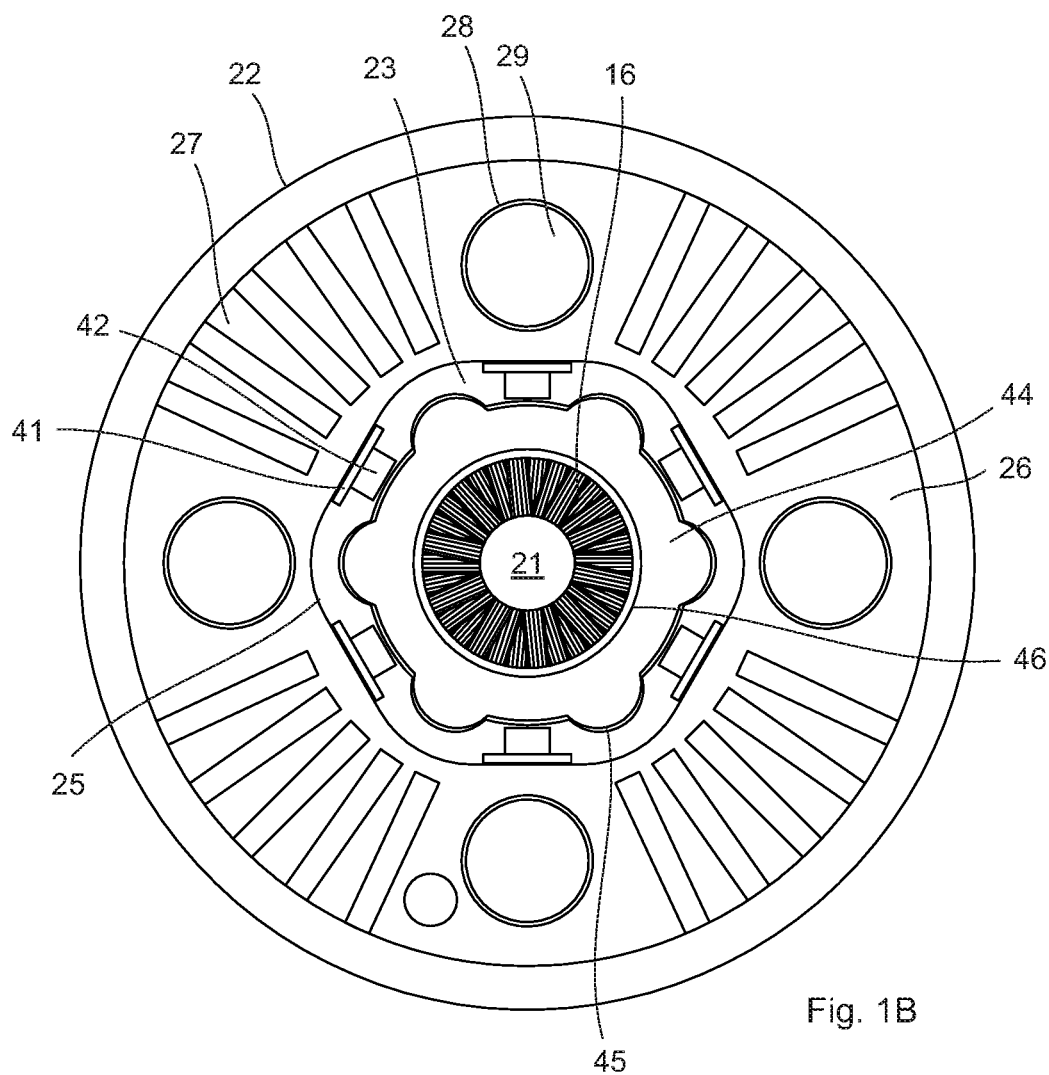
FIG. 1B illustrates a cross-section A-A of the device of FIG. 1A.

FIGS. 1A and 1B show a sideview of an embodiment of a sanitizing device and its cross-section along line A-A. In an embodiment the sanitizing device consists of three main parts, namely a brush assembly 10, main body 20 and coupler 30. By looking at the cross-section in FIG. 1B, a channel 21 can be seen in the middle and the channel 21 runs through the whole sanitizing device along a straight line. The main purpose of the sanitizing device is to sanitize a tube inserted in the channel 21 and running through the channel. Preferably the channel is in the middle or substantially in the middle of the sanitizing device. Preferably the channel has a circular or substantially circular shape allowing tubes to run smoothly through the channel.

Figure 2A:
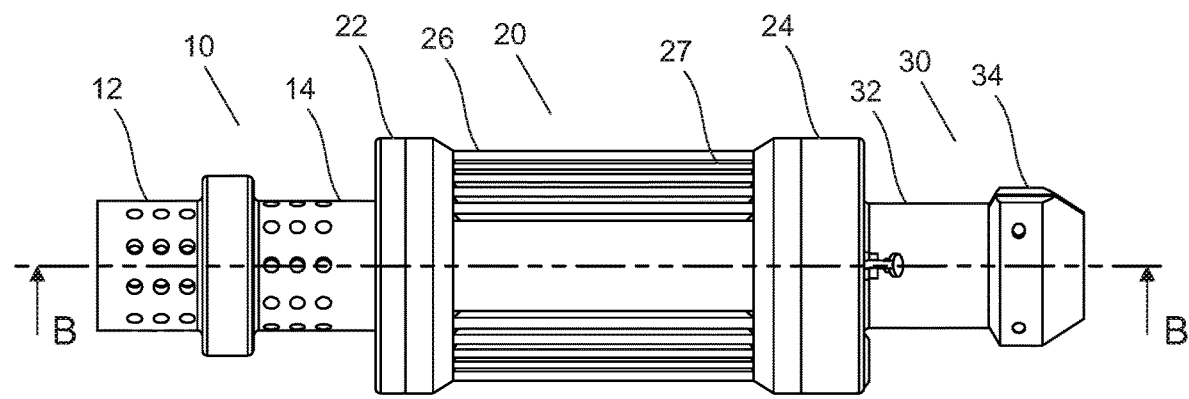
FIG. 2A shows a sideview of a sanitizing device according to an embodiment.
Figure 2B:
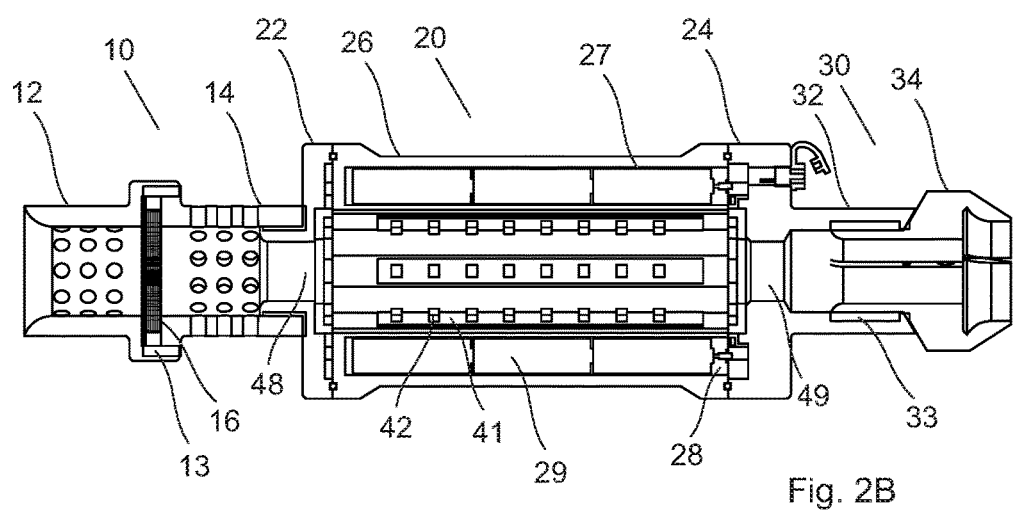
FIG. 2B illustrates a cross-section B-B of the device of FIG. 2A without a transparent tube.
Figure 2C:
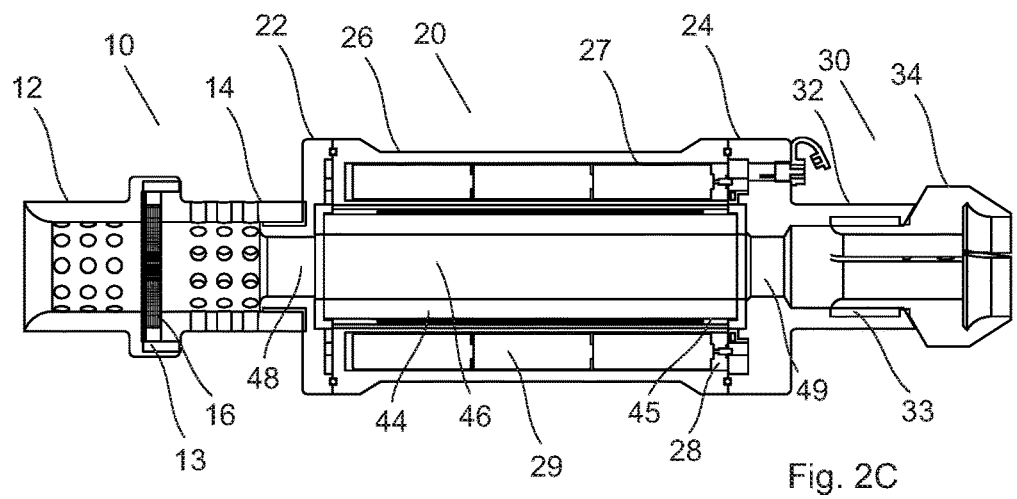
FIG. 2C illustrates a cross-section B-B of the device of FIG. 2A with a transparent tube.

In an embodiment, the channel is the smallest in diameter inside the brush assembly 10 where the channel 21 surrounded by bristles of a brush 16. Preferably the brush is an annular brush which has a ring-shaped frame and bristles 16 pointing radially inward from the inner surface of the ring-shaped frame. The brush is preferably located inside a perforated tube for facilitating cleaning of the brush. The perforated tube may consist of two parts, the first tube 14 and the second tube 12 which can be attached together by threaded sections 13 to form a longer tube as shown in FIG. 2B and FIG. 2C. Preferably both the first tube and the second tube have perforations. The annular brush may be in the first tube 14 or the second tube 12 or in both of said tubes in the threaded sections 13. Other brush configurations can also be used but the bristles of the brushes should encircle the channel 21 from all directions to properly clean a tube entering the main body 20. The bristles 16 of the brush are flexible yet stiff enough to scrape any deposits on a surface of a tube running through the brush assembly 10. The brush assembly 10 is preferably removably attached to first flange 22 of the main body 20.

On the opposite side of the main body 20 is a second flange 24. A tubular body 27 extends between the first flange 22 and the second flange 24. The coupler 30 is preferably removably attached to the second flange 24 of the main body 20. The coupler preferably consists of at least two parts: a first coupler part 32 and a second coupler part 34, which are preferably removably attached to each other, e.g. by threaded sections 33. In typical use situation, the first coupler part 32 is attached to the second flange 24 of the main body 20. The second coupler part 34 is attached to a machine with which the sanitizing device is being used. For quick removal of the sanitizing device, the first coupler part can be easily detached from the second coupler part which facilitates cleansing, recharging and transportation of the sanitizing device. The second coupler part 34 can remain attached to the machine so that attaching of the sanitizing device is faster next time. The second coupler part may also consist of several smaller parts depending on the shape of the part where the second coupler part is to be attached. Preferably the second coupler part is configured to be attached to a tubular shape, typically to a guide 120 controlling direction of a cable and cover tube used with the machine.

The main body 20 comprises the first flange 22 and the second flange 24 and a tubular body 26 extending between said flanges 22, 24. The first flange and the second flange can be integral parts at the ends of the tubular body 26 or they can be attached to the tubular body 26. The first flange and the second flange may or may not have an outer diameter larger the outer diameter of the tubular shape. The term flange does not refer so much to a shape of the flange but rather to its functionality as being at the ends of the tubular shape and being the part which connects the brush section 10 and the coupler 30 to the main body. The first flange and the second flange may have tubular sections 48, 49 which facilitate aligning of the brush section 10 and the coupler 30 with the main body 20.

FIGS. 1B and 2B illustrate cross-sections in different planes of the tubular body 26 and show parts inside it. The cross-section of FIG. 1B is shown towards the brush section 10 so the first flange 22 can be seen having larger diameter than the tubular body 26 in this embodiment. There are six strips 41 of ultraviolet light emitting diodes (UV LEDs) 42 arranged symmetrically on the inner surface 25 of the tubular body 26. The strips 41 can comprise only leads to the UV LEDs or the strips can also comprise resistors for the UV LEDs. In an embodiment, the strips 41 are circuit boards comprising all the needed passive and active components, including the UV LEDs. In an embodiment, the strips 41 can be omitted and the UV LEDs are then fixed directly to the inner surface 25 of the tubular body 26 and separate power wires are used for delivering power to the UV LEDs 42. The number of UV LEDs 42, both in circumferential direction and longitudinal direction, can be altered depending on the type of UV LEDs, shape of lens on the UV LED chips, size of the channel 21 and other characteristics. However, the UV LEDs should illuminate the channel 21 from all directions so that a tube moving through would receive germicidal ultraviolet irradiation substantially evenly to its outer surface. For example, in circumferential direction there can be four to ten UV LEDs and in longitudinal direction 1 to 20 UV LEDs, preferably 6 to 10 UV LEDs.

The UV LEDs are preferably emitting UVC radiation, i.e. in wavelengths from 100 nm to 280 nm. Preferably the peak output of the UV LEDs is in the range of 240 to 280 nm, more preferably from 250 to 270 nm, for example 254 nm or 265 nm.

In a preferred embodiment heat produced by the UV LEDs 42 is conducted to the tubular body 26 which then dissipates the heat into surrounding air through its outer surface. Preferably there are fins 27 on the outer surface of the tubular body 26 to increase surface area of the tubular body, thereby increase heat dissipation. The tubular body 26 is preferably made of metal for effectively conducting heat of the UV LEDs to the outer surface of the tubular body.

The tubular body 26 can also comprise one or more cavities 28 for accommodating batteries 29 that supply electric power to the UV LEDs 42. The cavities can also be through holes of the tubular body 26 such that the batteries 29 are held in place by first flange 22 and second flange 24 or some other part of the sanitizing device. Preferably the batteries 29 can be recharged without removing them from the sanitizing device. The batteries 29 should be chosen so that they can withstand the heat of the tubular body.

FIGS. 1B and 2C show a transparent tube 44 inside the tubular body 26 of the main body 20. The transparent tube is substantially transparent to the ultraviolet light emitted by the UV LEDs 42. Substantially transparent can mean that e.g. more than 80% transmission, more than 90% transmission or more than 95% transmission of the UV light produced by the UV LEDs. The transparent tube 45 protects the UV LEDs from mechanical damage when inserting a cable or a tube through the sanitizing device. The transparent tube also prevents any unwanted liquids or solids from getting into contact with the UV LEDs 42. Also cleaning of the insides of the sanitizing device can be performed by simply rinsing the channel 21 since the transparent tube protects the UV LEDs. Various plastic-based and glass-based materials can be used taking into account UV light transmission in the material.

The inner surface 25 of the tubular body and the outer surface 45 of the transparent tube 44 form a space between them where the strips 41 of UV LEDs 42 are located. The transparent tube 44 can be held in place inside the tubular body 26 by seal 23 at both ends of the transparent tube 44. The seal 23 is preferably an elastic seal made of e.g. silicone or similar material, so that the seal closes the gap between the inner surface 25 of the tubular body and the outer surface 45 of the transparent tube 44 at both ends of the transparent tube. This prevents any leaks to the space where the UV LEDs are located. An elastic seal surrounding the outer surface 45 of the transparent tube also increases tolerance of the sanitizing device for impacts, e.g. when the sanitizing device is accidentally dropped. Because of the elastic seal 23, also wiring to the strips 41 or UV LEDs 42 can be made through the same gap that the elastic seal 23 seals. In an embodiment, the first flange 22 and the second flange 24 of the main body 20, washers and gaskets can also be used for positioning the transparent tube and for sealing the space where the UV LEDs are located. The inner surface 46 of the transparent tube 44 defines the channel 21 inside the main body 20. The diameter of the inner surface 46 of the transparent tube 44 should be slightly larger than outer diameter of a tube that is intended to be sanitized with the sanitizing device.

Figure 3:
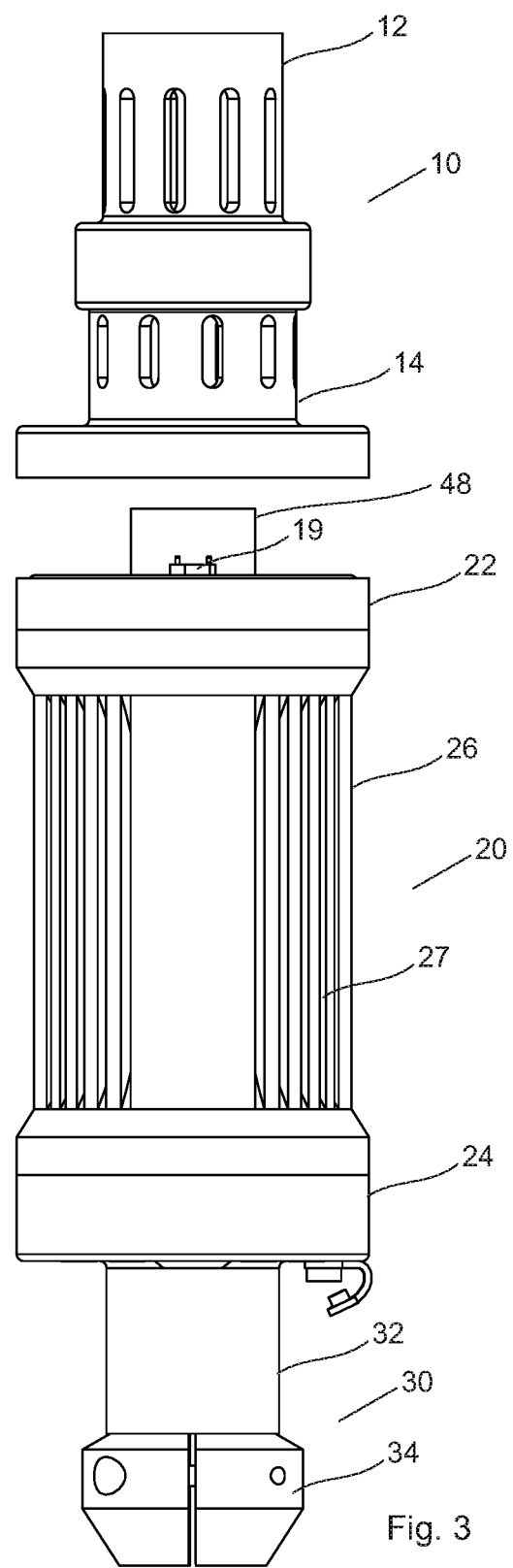
FIG. 3 shows a sideview of a sanitizing device according to an embodiment having a brush assembly detached.

FIG. 3 shows a sideview of a sanitizing device according to an embodiment having a brush assembly 10 detached from the main body 20. Similarly, the coupler 30 can be detached from the main body 20. When the brush assembly 10 is detached from the main body 20, the UV LEDs can be seen from outside the sanitizing device. In order to protect users from UV light, the sanitizing device preferably comprises a switch 19 which automatically turns off power from the UV LEDs when the brush section 10 is detached from the main body 20. The same arrangement can be used with the coupler 30.

In an embodiment the sanitizing device has a channel 21 through the sanitizing device. The sanitizing device comprises a coupler 30 for attaching the sanitizing device to a tubular shape, and a tubular body 26 having a plurality of ultraviolet LEDs 42 on its inner surface 25. The sanitizing device further comprises a transparent tube 44 at least partially inside said tubular body 26, wherein said plurality of ultraviolet LEDs 42 are arranged to a space between the inner surface 25 of the tubular body 26 and the outer surface 45 of the transparent tube 44.

Figure 4:
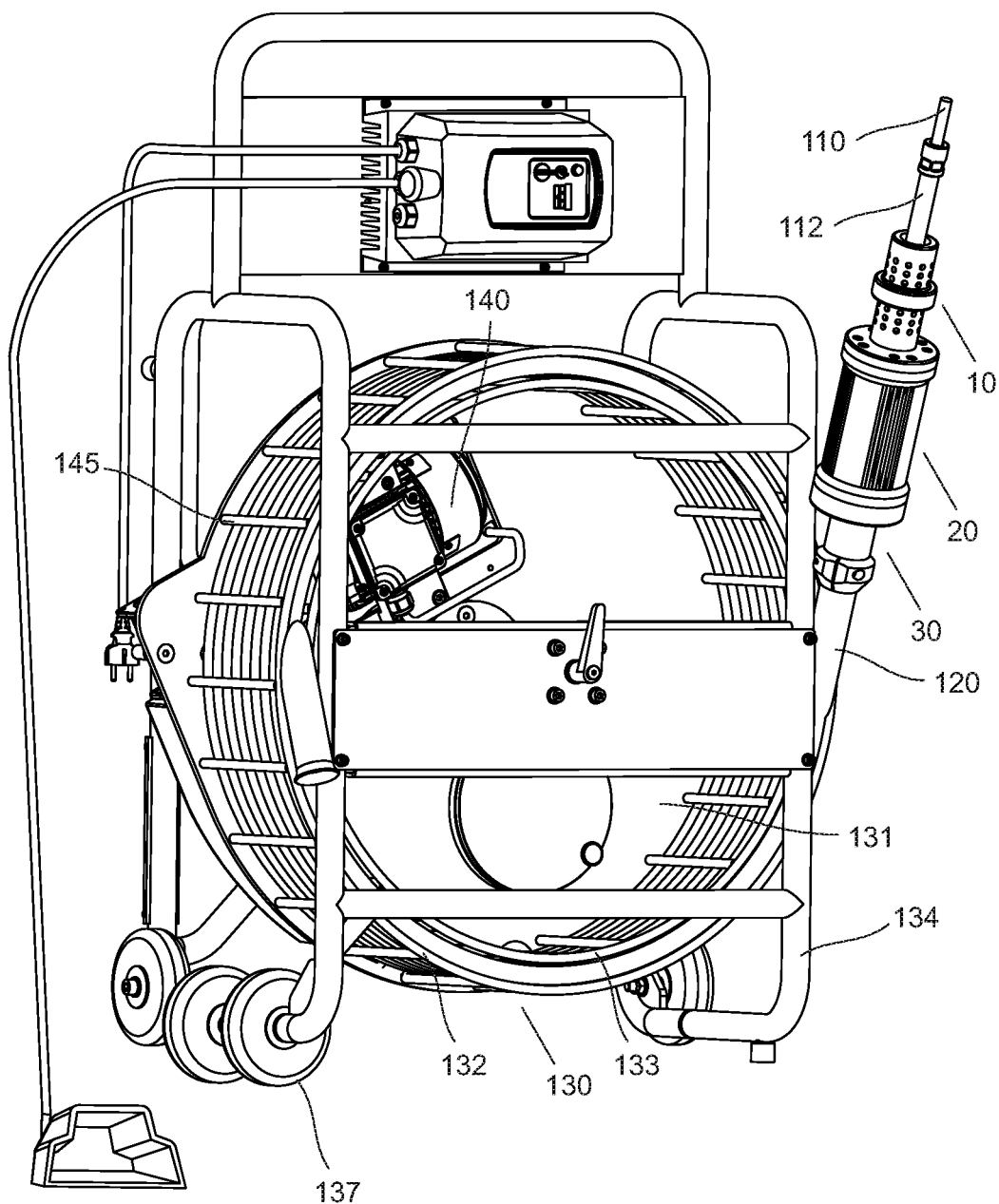
FIG. 4 shows a system comprising a sanitizing device according to an embodiment of the invention.
Figure 5:
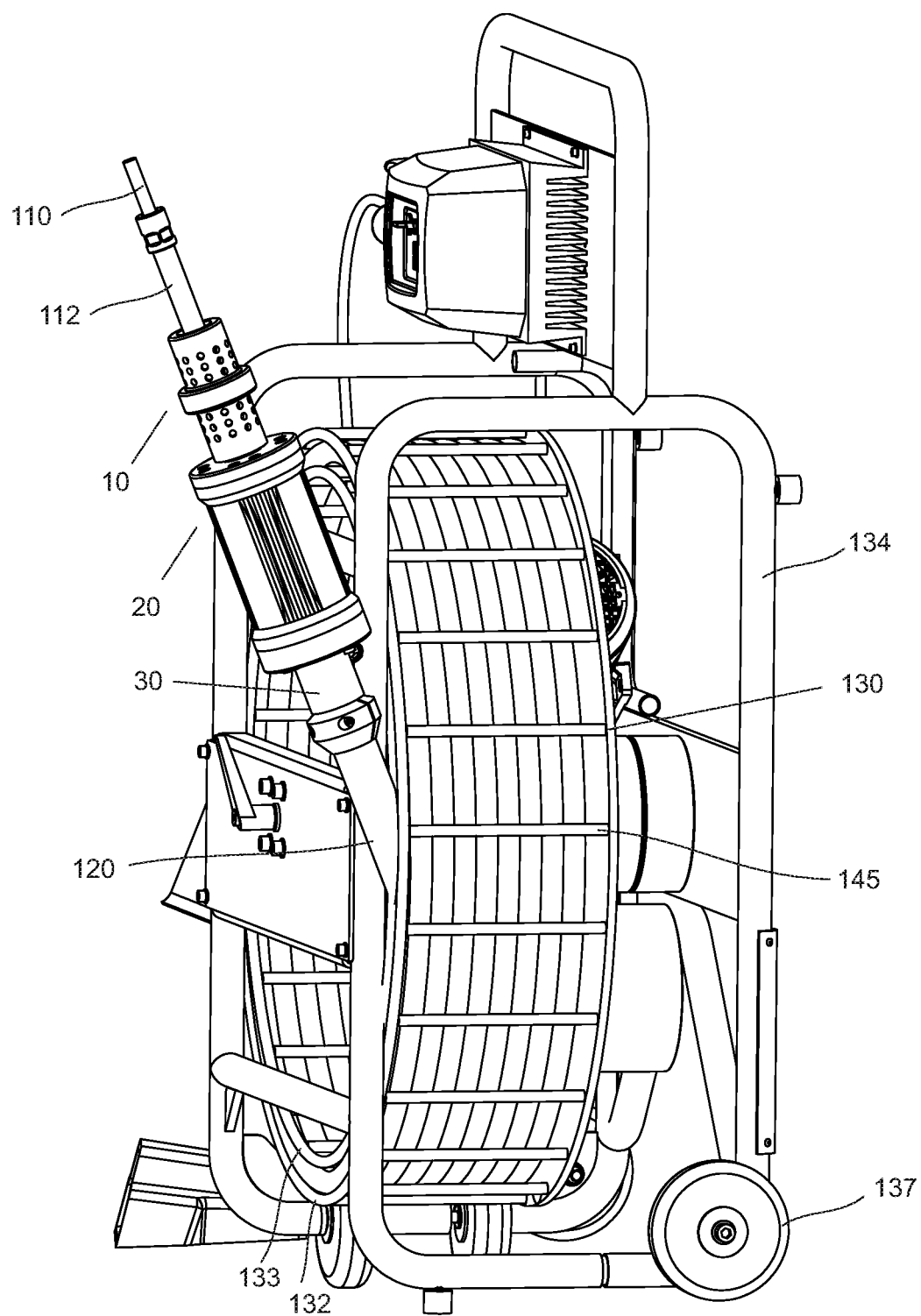
FIG. 5 shows the system shown in FIG. 3 from a different angle.

FIGS. 4 and 5 show a system comprising an embodiment of the sanitizing device of the present disclosure and a power transmission device, such as a sewer cleaning machine. The power transmission device according to an embodiment has a frame 134, which is preferably light and durable, for example, made of metal pipes or metal bars. The frame is preferably carriage-like and, in connection with it, there are wheels 137 to facilitate moving the device. In connection with the frame, there is arranged a reel 130, which can be rotated about an axle. The axle can be bearing-mounted, in order that the reel rotates more easily.

The power transmission device comprises a cable 110, and a cover tube 112 at least partially surrounding the cable 110. The cable is preferably a wound steel cable and the thickness of the cable may be, for example, 8, 10, 12, 14, 16, 18 or 21 mm or some other thickness appropriate for the intended use. In place of the cable, some other flexible, but torsionally rigid means may also be used. With the exception of its open heads, the cable 110 is inside the cover tube 112, within which the cable 110 is able to rotate as needed. At the tail end of the cable, there can be means for attaching a tool to the cable. The cover tube is of a flexible material, such as plastic, rubber or a mixture thereof. The cable 110 travels through the guide 120, which is, for example, a short tube. The sanitizing device of the present disclosure can be attached to the guide 120 by the coupler 30 of the sanitizing device. Thus, the cover tube 112 always runs through the sanitizing device when the cable is pulled from the reel or pushed into the reel. When a job is finished, it is preferable to slowly pull out all of the cable on the reel and slowly push it back on the reel again to treat the whole cover tube and reduce the number of bacteria as much as possible.

The reel 130 has an outer ring 132 and an inner ring 133, wherein the cable with its cover tube can be reeled into the space between the inner and outer rings. The power transmission device also comprises a guide 120 for feeding the cable onto and/or off the reel, and an electric motor 140 in connection with the head end of the cable 110 for rotating the cable. In an embodiment the rotation axle of the reel 130 is arranged substantially perpendicular in relation to its base onto which the device is placed when the device is in the operating position.

Preferably, the difference between the radii of the outer ring 132 and inner ring 133 of the reel 130 is less than double in relation to the diameter of the cover tube 112, so that two ducts cannot fit side-by-side but a cover tube being reeled in always sets on top of the previous layer. Thus, the cover tube cannot become jammed onto the reel but it moves easily onto the reel and can also be easily pulled off the reel. The combination of the cable and cover tube is preferably rigid enough that, as it is pushed onto the reel, the reel rotates in response to the cable being pushed onto the reel. This makes the device especially easy to use and enables a single person to operate the device, even at some distance from the frame and reel themselves. The inner and outer rings of the reel have preferably rungs 145 that keep the wire and cover tube substantially between the inner and outer rings. In place of the rungs, a disc-like solution may also be used.

In the inner portion 131 of the reel, there is the electric motor 140, which is attached either directly to the reel or to its baseplate such that the electric motor rotates along with the reel. The lowermost layer of the cover tube in the reel is turned inside the reel and the head end of the cable is arranged to be attached to the electric motor 140. As the electric motor rotates the head end of the cable, the cable 110 rotates within the cover tube and, at the same time, rotates a tool (not shown) attached to the tail end of the cable. In connection with the head end of the cable, there is preferably a safety switch, which breaks or opens if torsion grows too high, for example, as a result of the cable becoming jammed. The safety switch prevents additional damage by disconnecting the cable from the electric motor. Disconnection may be implemented by physically detaching the cable from the electric motor or by preventing the transmission to the cable of the rotational movement of the electric motor or a part thereof.

An embodiment of the present disclosure is therefore a system comprising a power transmission device which comprises a cable 110, and a cover tube 112 at least partially surrounding the cable, a reel 130 arranged to be rotated, into which the cable with its cover tube can be reeled, a guide 120 for feeding the cable onto and/or off the reel, and an electric motor 140 in connection with the head end of the cable 110 for rotating the cable. The system further comprises the sanitizing device of the present disclosure. In an embodiment the sanitizing device has a channel 21 through the sanitizing device, which sanitizing device comprises a coupler 30 for attaching the sanitizing device to a tubular shape, and a tubular body 26 having a plurality of ultraviolet LEDs 42 on its inner surface 25. The sanitizing device being further comprises a transparent tube 44 at least partially inside said tubular body 26, wherein said plurality of ultraviolet LEDs 42 are arranged to a space between the inner surface 25 of the tubular body 26 and the outer surface 45 of the transparent tube 44. In the system, said sanitizing device is attached to the guide 120 of the power transmission device.

In an embodiment of the system of the present disclosure, the electric motor 140 is attached to the inner portion 131 of the reel 130 and arranged to rotate along with the reel.

In an embodiment of the system of the present disclosure said reel 130 arranged to be rotated has an outer ring 132 and an inner ring 133, wherein the cable 110 with its cover tube 112 can be reeled into the space between the inner and outer rings. Preferably the difference between the radii of the outer ring 132 and the inner ring 133 of said reel 130 is less than double in relation to the diameter of the cover tube 112.

It is obvious to the skilled person in the art that, as technology develops, the basic idea of the invention can be implemented in various ways. The invention and its embodiments are therefore not limited to only the examples presented above, rather they may vary within the scope of the claims.

While the present invention has been described in accordance with preferred compositions and embodiments, it is to be understood that certain substitutions and alterations may be made thereto without departing from the spirit and scope of the following claims.

The invention claimed is:

1. A system having a power transmission device, comprising:
    a cable and a cover tube at least partially surrounding the cable,
    a rotatable reel into which the cable and the cover tube are being reelable,
    a guide in operative engagement with the cable and the reel,
    an electric motor being disposed at a head end of the cable,
    a sanitizing device attached to the guide, the sanitizing device having a channel defined therethrough and comprising a coupler, a tubular body in operative engagement with the coupler, the tubular body having a plurality of ultraviolet light-emitting diodes (LEDs) on an inner surface of the tubular body, and
    a transparent tube being disposed at least partially inside said tubular body, said plurality of ultraviolet LEDs being disposed between the inner surface of the tubular body and an outer surface of the transparent tube.

2. The system according to claim 1, wherein said electric motor is attached to an inner portion of the reel, the electric motor being rotatable along with the reel.

3. The system according to claim 1, wherein said reel is rotatable and has an outer ring and an inner ring, the outer ring and the inner ring having a space defined therebetween, wherein the cable and the cover tube are being reelable into the space between the inner and outer rings.

* * * * *